US012719520B2

(12) United States Patent
Monge et al.

(10) Patent No.: US 12,719,520 B2
(45) Date of Patent: Aug. 25, 2026

(54) DUAL-BAND TRANSCEIVER WITH MUTUALLY COUPLED ON-CHIP ANTENNAS FOR IMPLANTABLE/WEARABLE DEVICES

(71) Applicant: UNIVERSITY OF SOUTHERN CALIFORNIA, Los Angeles, CA (US)

(72) Inventors: Manuel Alejandro Monge, Los Angeles, CA (US); Nilan Udayanga Galabada Kankanamge, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 263 days.

(21) Appl. No.: 18/568,139

(22) PCT Filed: Jun. 9, 2022

(86) PCT No.: PCT/US2022/032761

§ 371 (c)(1),
(2) Date: Dec. 7, 2023

(87) PCT Pub. No.: WO2022/261271

PCT Pub. Date: Dec. 15, 2022

(65) Prior Publication Data

US 2024/0275420 A1 Aug. 15, 2024

Related U.S. Application Data

(60) Provisional application No. 63/208,864, filed on Jun. 9, 2021.

(51) Int. Cl.

*H04B 1/3827* (2015.01)
*A61B 5/00* (2006.01)

(Continued)

(52) U.S. Cl.

CPC ........... *H04B 1/385* (2013.01); *A61B 5/0031* (2013.01); *A61N 1/37223* (2013.01); *H04B 1/005* (2013.01)

(58) Field of Classification Search

CPC ...... H04B 1/385; H04B 1/005; A61B 5/0031; A61B 5/021; A61B 5/024; A61B 5/03;

(Continued)

(56) References Cited

U.S. PATENT DOCUMENTS

| | | | | |
|---|---|---|---|---|
| 6,434,194 | B1 | 8/2002 | Eisenberg et al. | |
| 12,121,336 | B2 * | 10/2024 | Leabman ........... | A61B 5/02108 |

(Continued)

OTHER PUBLICATIONS

Mirbozorgi SA, Bahrami H, Sawan M, Rusch LA, Gosselin B. A single-chip full-duplex high speed transceiver for multi-site stimulating and recording neural implants. IEEE transactions on biomedical circuits and systems. Oct. 12, 2015;10(3):643-53. (Year: 2016).*

Int'l Search Report and Written Opinion mailed Aug. 30, 22 for PCT Appn. No. PCT/US22/32761 filed Jun. 9, 22, 9 pgs.

*Primary Examiner* — Fayyaz Alam
(74) *Attorney, Agent, or Firm* — Brooks Kushman P.C.

(57) ABSTRACT

A dual-band implantable/wearable transceiver includes a first on-chip antenna and a second on-chip antenna that are mutually coupled. A receiver includes a dual receiver chain having a first receiver chain and a second receiver chain. The first receiver chain is in electrical communication with the first on-chip antenna and configured to operate within a first frequency band. Similarly, the second receiver chain is in electrical communication with the second on-chip antenna and configured to operate within a second frequency band. A dual-band dual-port LC oscillator-based transmitter is in electrical communication with the first on-chip antenna and the second on-chip antenna and configured transmit data within the first frequency band and/or the second frequency band. A power management unit is configured to supply (Continued)

power to the receiver and the dual-band dual-port LC oscillator-based transmitter.

22 Claims, 11 Drawing Sheets

(51) Int. Cl.
*A61N 1/372* (2006.01)
*H04B 1/00* (2006.01)

(58) Field of Classification Search
CPC ..... A61B 5/318; A61B 5/0015; A61B 5/6802; A61B 5/686; A61B 2560/0209; A61N 1/37223; A61N 1/36014; A61N 1/3787; A61N 1/37229; A61N 1/378
See application file for complete search history.

(56) References Cited

U.S. PATENT DOCUMENTS

2007/0260293 A1 11/2007 Carpenter et al.
2007/0288066 A1* 12/2007 Christman ............... H01Q 1/38 607/32
2008/0129630 A1* 6/2008 Baliarda .................. H01Q 1/36 343/873
2010/0099367 A1* 4/2010 Shamim .............. H10F 39/1892 455/95
2019/0286592 A1* 9/2019 Seo .......................... A61B 5/24
2020/0014330 A1* 1/2020 Bushman ................. H03B 5/12
2021/0050868 A1* 2/2021 Weissman ................ H04B 1/18
2022/0247077 A1* 8/2022 Bhagavatula ............ H04B 1/44
2024/0356594 A1* 10/2024 Nabki .................. H04B 7/0479
2025/0213872 A1* 7/2025 Pivonka ................. G16H 40/63

* cited by examiner

DUAL-BAND TRANSCEIVER WITH MUTUALLY COUPLED ON-CHIP ANTENNAS FOR IMPLANTABLE/WEARABLE DEVICES

This application is the U.S. national phase of PCT Appln. No. PCT/US2022/032761 filed Jun. 9, 2022, which claims the benefit of U.S. provisional application Ser. No. 63/208,864 filed Jun. 9, 2021, the disclosures of which are hereby incorporated in their entirety by reference herein.

STATEMENT REGARDING FEDERALLY SPONSORED RESEARCH OR DEVELOPMENT

This invention was made with government support under EB030244 awarded by the National Institutes of Health. The government has certain rights in the invention.

TECHNICAL FIELD

In at least one aspect, the present invention relates to implantable and wearable devices with increased efficiency and reduced size.

BACKGROUND

Recent progress in implantable and wearable technologies has made them an important tool for physicians to monitor biophysical parameters, diagnose numerous health conditions, and treat diseases. Applications of such devices include drug delivery systems, neural interfaces, vital sign sensors, and intraocular pressure sensors [1]-[3]. Implantable and wearable devices demand low power consumption, small form factor (mm-scale), and wireless connectivity. In such devices, the transceiver (TRX) dominates the overall power (data transmission) and area (passive components and antenna) consumption. Thus, the main goal in designing implantable/wearable transceivers (IWTs) is to achieve a high data rate and communication range with less power and area. Current single-band IWTs achieve Mb/s of data rates and pJ/bit of energy efficiencies for cm-scale communication ranges [4]-[7].

Most medical devices currently operate at 400-430 MHz or at 900-915 MHZ (due to less absorption by body tissues), whereas most consumer electronics such as mobile phones and smartwatches support 2.4 GHz. This mismatch between medical devices and consumer electronics hinders their natural communication ability and requires additional components to create a full system solution. The resulting sub-optimal system can be bigger, less efficient, and can limit otherwise possible biomedical applications. In addition, most of the existing IWTs have used off-chip antennas to improve the communication range by trading off the size of the complete system [4]-[6].

Accordingly, there is a need for improved Implantable and wearable devices with increased efficiency and reduced size.

SUMMARY

In at least one aspect, a dual-band implantable/wearable device is provided. dual-band implantable/wearable device includes a transceiver. The transceiver includes a first on-chip antenna and a second on-chip antenna that are mutually coupled. A receiver includes a dual receiver chain having a first receiver chain and a second receiver chain. The first receiver chain is in electrical communication with the first on-chip antenna and configured to operate within a first frequency band. Similarly, the second receiver chain is in electrical communication with the second on-chip antenna and configured to operate within a second frequency band. A dual-band dual-port LC oscillator-based transmitter is in electrical communication with the first on-chip antenna and the second on-chip antenna and configured to transmit data within the first frequency band and/or the second frequency band. A power management unit is configured to supply power to the dual-band dual-port LC oscillator-based transmitter. The device can also include a circuit board attached transceiver, the circuit board including any combination of external sensors, capacitors, controller units, and a single battery.

In another aspect, the dual-band implantable/wearable device is configured for the simultaneous transmission and/or reception both frequency bands. For example, the transceiver can simultaneously transmit at 915 MHz and 2.4 GHz frequency bands. Similarly, it can receive simultaneously from both bands.

In another aspect, a system for monitoring a subject is provided. The system includes the dual-band implantable/wearable device as described herein. At least one external device is attached to the subject and in electrical communication (e.g., wireless communication) with the dual-band implantable/wearable device.

In another aspect, a 2.4×1.9 mm$^2$ dual-band IWT addresses the limitations of the prior art by operating at 915 MHz and 2.4 GHz in both transmit and receive modes and achieving cm-range bidirectional communication using on-chip antennas. The TRX provides a unique connecting platform between medical and consumer electronics in a single chip and enables a wide variety of applications, including implantable and wearable devices, body area networks, and health monitoring systems. For IWTs, the data rate requirement for uplink (TRX to an external system) and downlink (external system to TRX) is usually asymmetric. Higher data rates are required for uplink (to support multi-channel sensor data as in neural recording) than downlink (only controlling and actuation signals) [1]. The IWT uses this information to minimize its power and area consumption. It achieves up to 38 cm and 17 cm of communication distance and maximum data rates up to 40 Mb/s and 2 Mb/s for the uplink and downlink, respectively, with less than 70 pJ/bit of energy efficiencies.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

For a further understanding of the nature, objects, and advantages of the present disclosure, reference should be made to the following detailed description, read in conjunction with the following drawings, wherein like reference numerals denote like elements and wherein.

DETAILED DESCRIPTION

Figure 1A:
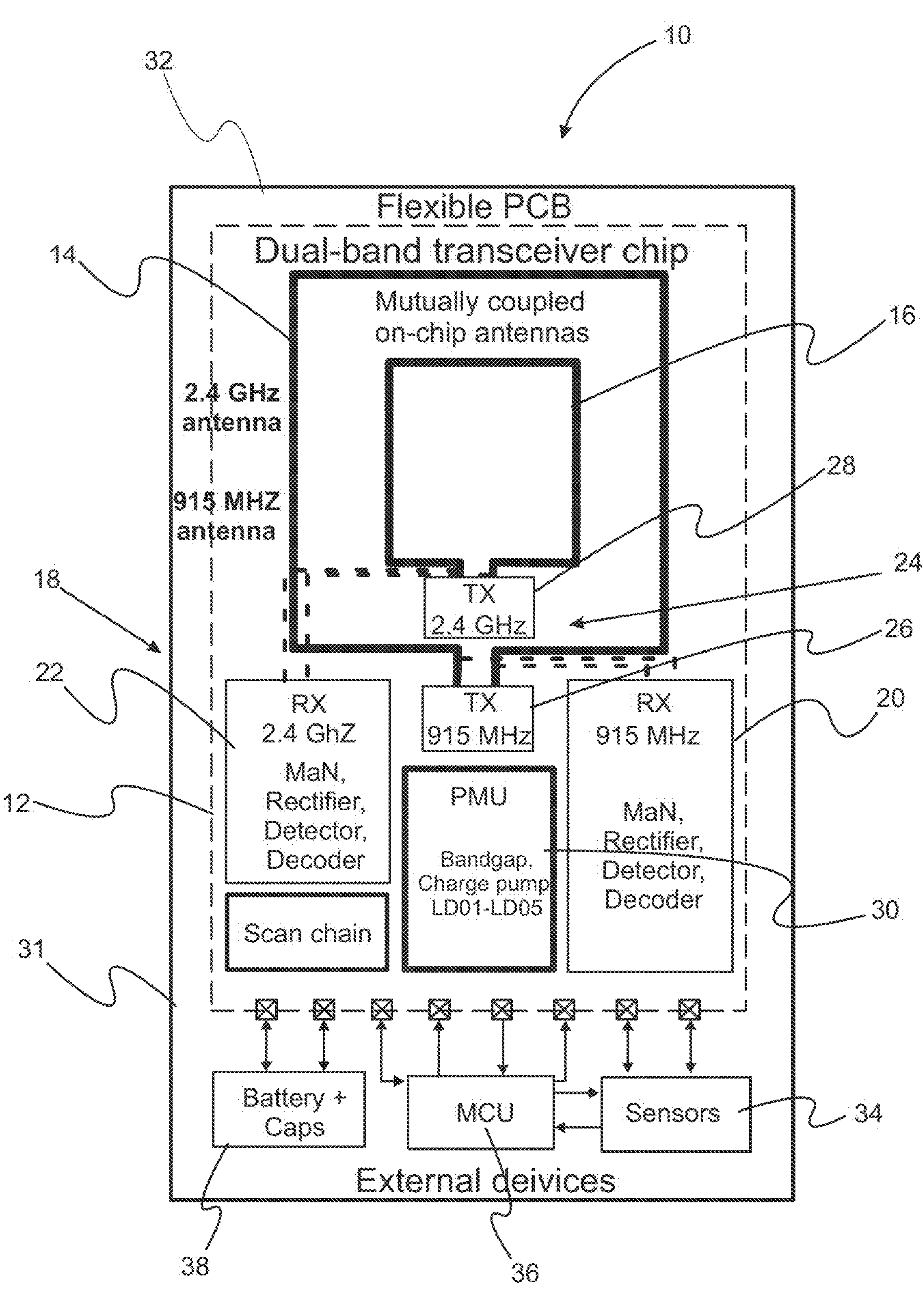
FIG. 1A: Schematic of a dual-band implantable/wearable device.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

When referring to a numerical quantity, in a refinement, the term "less than" includes a lower non-included limit that is 5 percent of the number indicated after "less than." A lower non-includes limit means that the numerical quantity being described is greater than the value indicated as a lower non-included limited. For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, 1 percent, or 0 percent of the number indicated after "less than."

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For any device described herein, linear dimensions and angles can be constructed with plus or minus 50 percent of the values indicated rounded to or truncated to two significant figures of the value provided in the examples. In a refinement, linear dimensions and angles can be constructed with plus or minus 30 percent of the values indicated rounded to or truncated to two significant figures of the value provided in the examples. In another refinement, linear dimensions and angles can be constructed with plus or minus 10 percent of the values indicated rounded to or truncated to two significant figures of the value provided in the examples.

With respect to electrical devices, the term "connected to" means that the electrical components referred to as connected to are in electrical communication. In a refinement, "connected to" means that the electrical components referred to as connected to are directly wired to each other. In another refinement, "connected to" means that the electrical components communicate wirelessly or by a combination of wired and wirelessly connected components. In another refinement, "connected to" means that one or more additional electrical components are interposed between the electrical components referred to as connected to with an electrical signal from an originating component being processed (e.g., filtered, amplified, modulated, rectified, attenuated, summed, subtracted, etc.) before being received to the component connected thereto.

The term "electrical communication" means that an electrical signal is either directly or indirectly sent from an originating electronic device to a receiving electrical device. Indirect electrical communication can involve processing of the electrical signal, including but not limited to, filtering of the signal, amplification of the signal, rectification of the signal, modulation of the signal, attenuation of the signal, adding of the signal with another signal, subtracting the signal from another signal, subtracting another signal from the signal, and the like. Electrical communication can be accomplished with wired components, wirelessly connected components, or a combination thereof.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within +0%, 0.1%, 0.5%, 1%, 2%, 3%, 4%, 5% or 10% of the value or relative characteristic.

The term "electrical signal" refers to the electrical output from an electronic device or the electrical input to an electronic device. The electrical signal is characterized by voltage and/or current. The electrical signal can be stationary with respect to time (e.g., a DC signal) or it can vary with respect to time.

The terms "DC signal" refer to electrical signals that do not materially vary with time over a predefined time interval. In this regard, the signal is DC over the predefined interval. "DC signal" includes DC outputs from electrical devices and DC inputs to devices.

The terms "AC signal" refer to electrical signals that vary with time over the predefined time interval set forth above for the DC signal. In this regard, the signal is AC over the predefined interval. "AC signal" includes AC outputs from electrical devices and AC inputs to devices.

It should also be appreciated that any given signal that has a non-zero average value for voltage or current includes a DC signal (that may have been or is combined with an AC signal). Therefore, for such a signal, the term "DC" refers to the component not varying with time and the term "AC" refers to the time-varying component. Appropriate filtering can be used to recover the AC signal or the DC signal.

The term "electronic component" refers is any physical entity in an electronic device or system used to affect electron states, electron flow, or the electric fields associated with the electrons. Examples of electronic components include, but are not limited to, capacitors, inductors, resistors, thyristors, diodes, transistors, etc. Electronic components can be passive or active.

The term "electronic device" or "system" refers to a physical entity formed from one or more electronic components to perform a predetermined function on an electrical signal.

It should be appreciated that in any figures for electronic devices, a series of electronic components connected by lines (e.g., wires) indicates that such electronic components are in electrical communication with each other. Moreover, when lines directed connect one electronic component to another, these electronic components can be connected to each other as defined above.

The term "computing device" refers generally to any device that can perform at least one function, including communicating with another computing device. In a refinement, a computing device includes a central processing unit that can execute program steps and memory for storing data and a program code.

When a computing device is described as performing an action or method step, it is understood that the one or more computing devices are operable to and/or configured to perform the action or method step typically by executing one or more lines of source code. The actions or method steps can be encoded onto non-transitory memory (e.g., hard drives, optical drive, flash drives, and the like).

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in an executable software object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

Throughout this application, where publications are referenced, the disclosures of these publications in their entireties are hereby incorporated by reference into this application to more fully describe the state of the art to which this invention pertains.

ABBREVIATIONS

"IWT" means implantable/wearable transceivers.

"LC" means inductor capacitor.

"LNA" means low noise amplifier.

"MCU" means microcontroller unit.

"OOK-PWM" means on-off keying with pulse width modulation "OOK-PWM."

"PMU" means power management unit.

"TRX" means transceiver.

"TX" means transmitter.

"RX" means receiver.

Figure 1B:
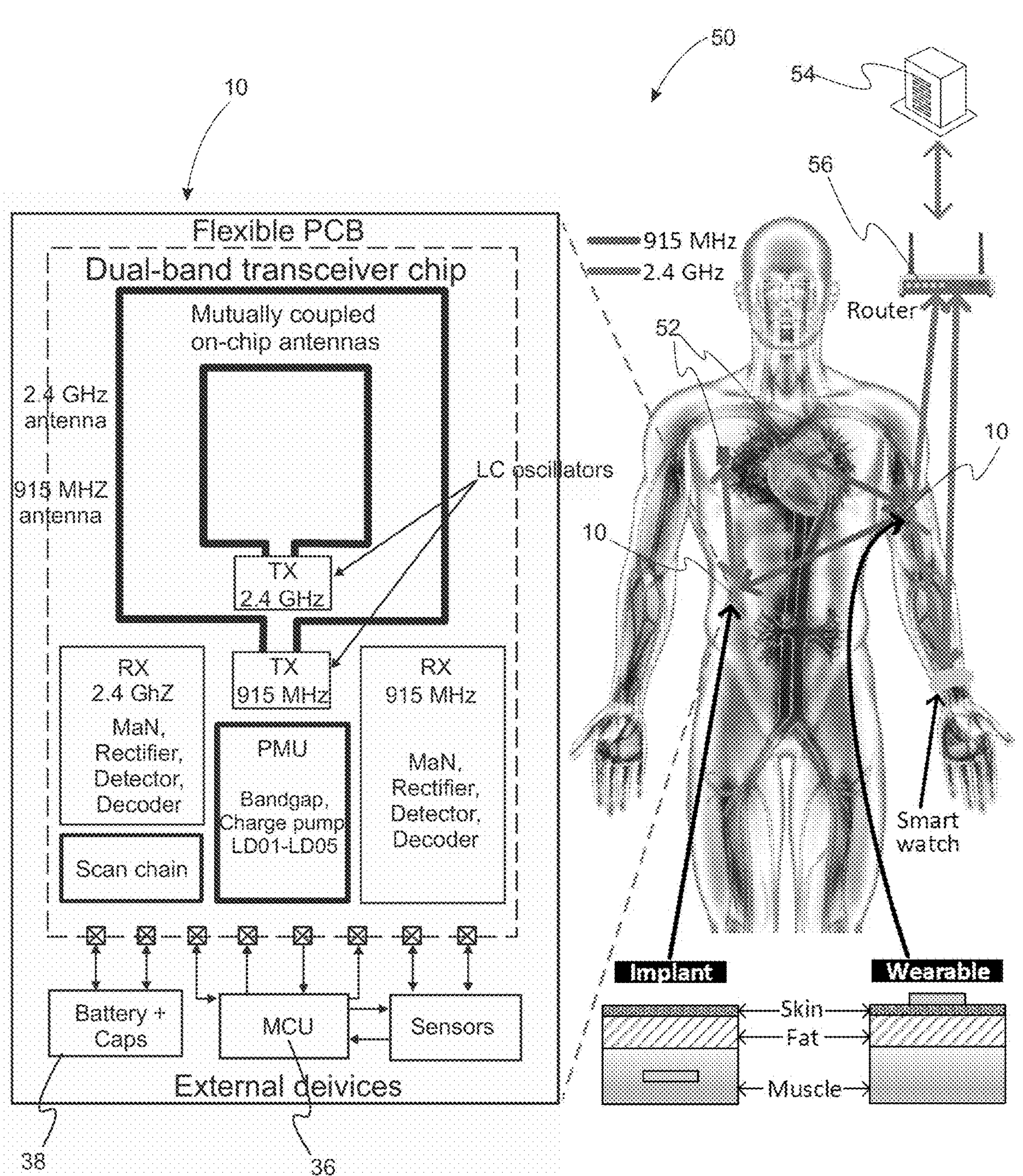
FIG. 1B: Left: System architecture of a dual-band TRX. Right: Intended applications of the TRX as an implant and wearable.

Referring to FIGS. 1A and 1B, a dual-band implantable/wearable device is provided. Advantageously, the dual-band implantable/wearable device can be implanted in or worn by a user. Dual-band implantable/wearable device 10 includes a transceiver 12 which includes a first on-chip antenna 14 and a second on-chip antenna 16. Characteristically, the first on-chip antenna 14 and the second on-chip antenna 16 are mutually coupled. A receiver 18 includes a dual receiver chain having a first receiver chain 20 and a second receiver chain 22. The first receiver chain 20 is in electrical communication with the first on-chip antenna 14 and configured to operate within a first frequency band. Similarly, the second receiver chain 22 is in electrical communication with the second on-chip antenna 16 and configured to operate within a second frequency band. In a refinement, the first frequency band is about 915 MHz and the second frequency band is about 2.4 GHz.

Transceiver 12 also includes a dual-band dual-port LC oscillator-based transmitter 24 which includes LC oscillators 26 and 28. Dual-band dual-port LC oscillator-based transmitter 24 is in electrical communication with the first on-chip antenna 14 and the second on-chip antenna 16. The dual-band dual-port LC oscillator-based transmitter 24 is configured to transmit data within the first frequency band and/or the second frequency band. Characteristically, the dual-band implantable/wearable transceiver 12 is configured to time-multiplex the first on-chip antenna 14 and the second on-chip antenna 16 to transmit and receive data. In a variation, the dual-band dual-port LC oscillator-based transmitter 24 includes a mutually coupled dual-band oscillator in which the first on-chip antenna and the second on-chip antenna operate as oscillator inductors. In a refinement, the dual-band dual-port LC oscillator-based transmitter directly feeds oscillator signals to the first on-chip antenna and the second on-chip antenna without using a separate power amplifier thereby reducing both the power consumption and chip area compared to a PA+oscillator architecture. In the example depicted, the first on-chip antenna 14 is drivn by oscillator 26 and the second on-chip antenna 16 is driven by oscillator 28.

In some applications, external devices (e.g., medical devices or consumer electronics) can request data using either the first frequency band or the second frequency band. Following the request, the chip-enabled device initiates the controlling signals to extract the sensing data from the external sensors. The extracted data can then directly modulate the transmitter 24 to communicate with the external system. The transceiver 12 supports both on-off keying with pulse width modulation (OOK-PWM) and standard OOK modulation. Similarly, the dual-band transceiver 12 can operate as a relay (or a hub) in-between other medical devices and smart mobile devices that only operate within either the first frequency band or the second frequency band.

Transciever 12 also includes a power management unit (PMU) 30 configured to supply power to the receiver and dual-band dual-port LC oscillator-based transmitter. In a variation, the power management unit 30 includes a bandgap reference, five low-dropout (LDO) regulators (LDO1 to LDO5), a charge pump, and a relaxation oscillator described below in more detail.

Dual-band implantable/wearable device 10 also includes a circuit board 32 (e.g., a flexible PCB) attached to transceiver 12. The circuit board includes any combination of external sensors 34, capacitors, controller units 36, and a single battery 38. The power management unit 30 is further configured to supply power to external sensors 34, actuators, and controller units 36.

Figure 2:
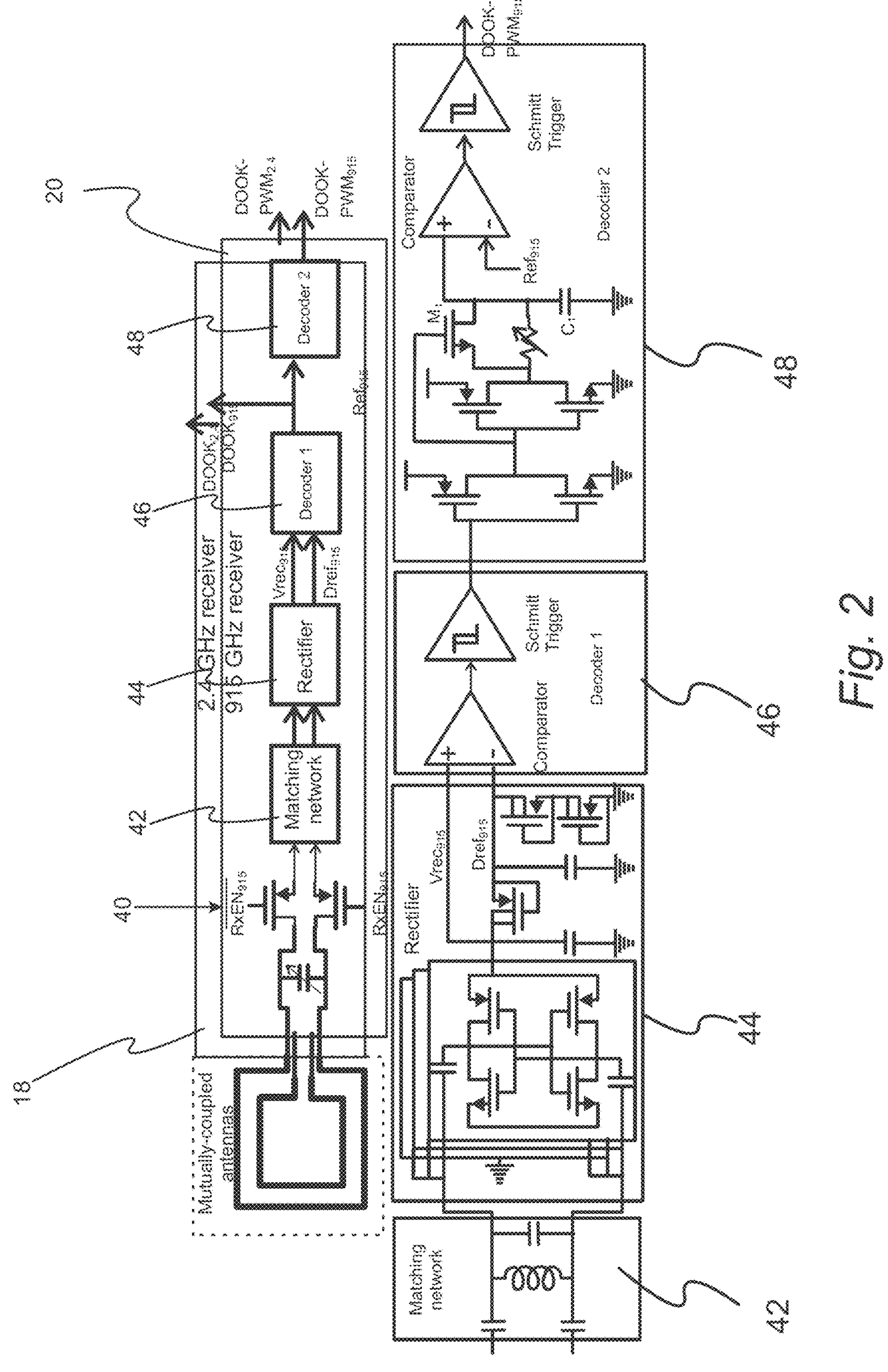
FIG. 2: Schematic of the dual-band receiver.

Referring to FIG. 2, a schematic of the receiver is provided. In a variation, the receiver is a rectifier-based receiver. As set forth above, the receiver includes a dual receiver chain having a first receiver chain 18 and a second receiver chain 20. The first receiver chain 18 and the second receiver chain 20 each independently include a switch 40, a matching network 42, a rectifier 44, a first decoder 46, and a second decoder 48 arranged in the order indicated and in electrical communication. Characteristically, each rectifier 44 is a cascade of four cross-connected differential rectifiers. Typically, OOK data is recovered at first decoder 46 by comparing rectified output with a dynamic reference generated by averaging this output using a low-pass filter with a Schmitt-trigger following the comparator to decrease noise sensitivity. For OOK-PWM, an output of the first decoder 46 is fed into the second decoder 48 to be first integrated throughout a pulse width and then compared with a predefined threshold voltage, a comparator in the second decoder outputs '1' or '0' based on integrated pulse duration.

In a variation, transceiver 11 is configured to be interconnected with external sensors 34, capacitors, controller units 36, and a single battery 38. Dual-band implantable/wearable device 10 is configured such that external devices can request data using either the first frequency band or the second frequency band. In a refinement, an external control unit is configured to initiate controlling signals to extract sensing data from external sensors following a request for data, wherein extracted data directly modulates the dual-band dual-port LC oscillator-based transmitter to communicate with external devices. In a further refinement, dual-band implantable/wearable device 10 is configured to support both on-off keying with pulse width modulation (OOK-PWM) and standard OOK modulation.

With reference to FIG. 1B, a schematic of a system for monitoring a subject is provided. System 50 includes the dual-band implantable/wearable device 10 as described above. At least one external device 52 is attached to the subject and in electrical communication (e.g., wireless communication) with the dual-band implantable/wearable device 10. In one refinement, the external device 52 is a drug delivery system. In another refinement, the at least one external device is a neural interface. In another refinement, the at least one external device is a blood pressure sensor, a heart rate sensor, an ECG, a vital sign sensors, and/or an intraocular pressure sensor. In a refinement, dual-band implantable/wearable device 10 is in electrical communication (e.g., wireless) with computing device 54. Router 56 can be used for this purpose.

The following examples illustrate the various embodiments of the present invention. Those skilled in the art will recognize many variations that are within the spirit of the present invention and scope of the claims.

I. Mutually-Coupled Dual-Band Transceiver

As set forth above, FIG. 1B shows the block diagram of the dualband TRX with power management unit (PMU). The CMOS chip consists of two mutually-coupled antennas, a dual-band dual-port LC oscillator-based transmitter (TX), rectifier-based receivers (RXs), a PMU, and a scan chain. The fabricated chip can be interconnected on a flexible printed circuit board (PCB) with external sensors, capacitors, controller units and a single battery to be used as an implantable/wearable medical device. The PMU generates the required supplies to power the internal TRX and external sensors, actuators, and controller units from a single battery. The TRX time multiplexes the antennas to transmit and receive data. In an intended application (see FIG. 1B), external devices (medical devices or consumer electronics) can request data using either frequency band. Following the request, the chip-enabled device initiates the controlling signals to extract the sensing data from the external sensors. The extracted data can then directly modulate the TX to communicate with the external system. The TRX supports both on-off keying with pulse width modulation (OOK-PWM) and standard OOK modulation. Similarly, the dual-band TRX can operate as a relay (or a hub) in-between other medical devices and smart mobile devices that only operate at either 915 MHz or 2.4 GHz frequency bands.

A. Mutually-Coupled On-Chip Antennas

Figure 3:
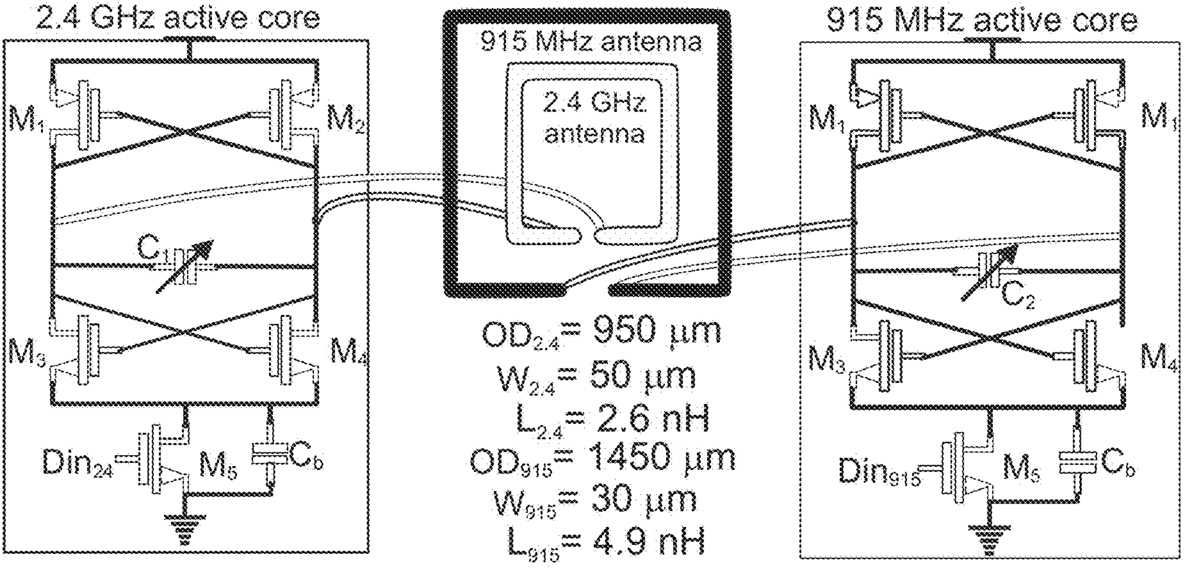
FIG. 3: Schematic of the dual-band dual-port LC oscillator with mutually coupled inductors (antennas).
Figure 4A:
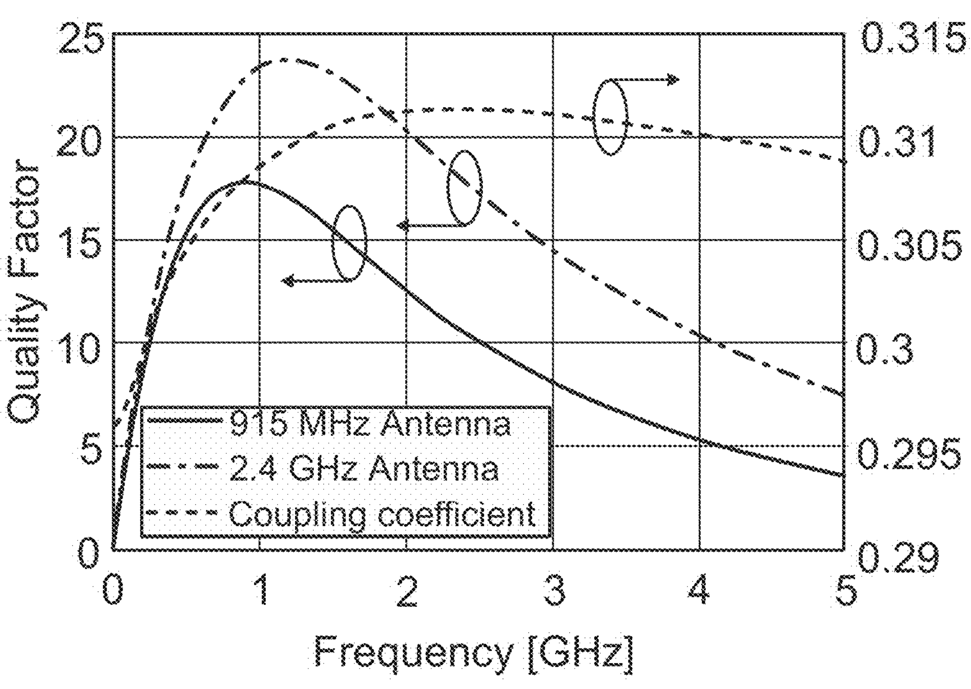
FIGS. 4A and 4B: (A) Variation of the quality factors of the individual loops when they are placed in a concentric configuration and the simulated coupling coefficient (k) of the designed mutually-coupled antennas. (B) The magnitude input impedance looking into the two ports with and without mutual coupling.

Two on-chip rectangular loops have been custom designed as the antennas of the TRX, and are also used as the inductors of the LC oscillators (FIG. 3). The two antennas are placed in a concentric configuration to reduce the chip area and are optimized to enhance the near-field coupling between them and the external system. Based on electromagnetic simulations through HFSS, the antennas exhibit 15-20 dB improved electric and magnetic fields at a distance of 5 cm away from the antenna, compared to a standard multi-turn inductor (outer diameter OD=410 m, 4 turns) with similar inductance. FIG. 3 shows the OD, width (W), and simulated inductances of the 915 MHz and 2.4 GHz antennas. FIG. 4(A) shows the variation of the quality factors of the individual loops in a concentric configuration, with both antennas exhibiting a quality factor (Q) 18 at their resonance frequencies.

B. Transmitter: Dual-Band Dual-Port Oscillator

Figure 4B:
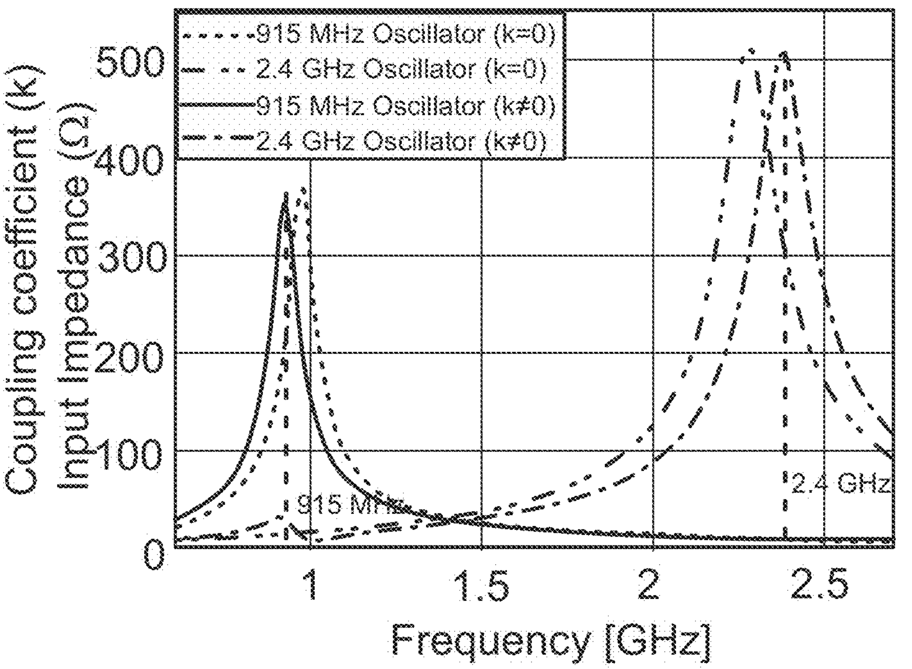

The TX (FIG. 3) directly feeds the oscillator signals to the antennas without using a separate power amplifier (PA), reducing both the power consumption and chip area compared to a PA+oscillator architecture. A fourth-order, dual-port resonator with separate LC tanks has been designed, where the two inductors (antennas) are placed in a concentric configuration. Their coupling coefficient (k) was kept less than 0.4 to sustain steady-state oscillation at both frequency bands [8], with a simulated value of 0.3 throughout the required frequency range (FIG. 4(A)). The geometry of the 2.4 GHz antenna is selected such that the impedance looking into its input port shows a higher peak than that of the 915 MHz antenna when k=0. This asymmetry allows having a sufficient peak at both frequencies when the two inductors are mutually coupled, even if k increases due to the changes in the surrounding environment (FIG. 4(B)). Capacitors C1 and C2 are realized using 3-bit capacitor arrays to compensate for PVT variations. The active core of the dual-band oscillator is designed using CMOS cross-coupled pairs powered by 1.2 V.

C. Receiver: Fully-Differential Full-Wave Rectifier

The receiver consists of a dual RX chain with a switch, a matching network, a rectifier, decoder 1 (DC1), and decoder 2 (DC2) per band (FIG. 2). A rectifier-based RX is selected because of its low power and area consumption compared to low noise amplifier (LNA)-based RX and the low data-rate requirements of IWTs. The passive gain of the matching network is important in the absence of an LNA to improve the sensitivity of the RX. The simulated passive gains of the 915 MHz and 2.4 GHz matching networks are 6.2 dB and 5.0 dB, respectively. The rectifier is a cascade of four cross-connected differential rectifiers. Low threshold voltage transistors are used to achieve a low turn-on voltage, which mainly determines the sensitivity of the RX. OOK data is recovered at DC1 by comparing the rectified output with a dynamic reference generated by averaging this output using a low-pass filter. A Schmitt-trigger follows the comparator to decrease noise sensitivity. For OOK-PWM, the output of DC1 is fed into DC2 to be first integrated throughout the pulse width and then compared with a predefined threshold voltage. The comparator in DC2 outputs '1' or '0' based on the integrated pulse duration.

D. Power Management Unit

The chip is powered by a single 1.5 V battery. The PMU consists of a bandgap reference, five low-dropout (LDO) regulators (LDO1 to LDO5), a charge pump, and a relaxation oscillator. The RX and TX supplies are generated using LDO1 (1 V) and LDO2 (1.2 V), respectively. Internal digital circuitry is powered by LDO3 (1.2 V). The external controller and sensors requiring 1.8 V supply are powered using LDO4 and LDO5. The bandgap employs a pre-regulator to achieve a PSRR of −60 dB at 1 MHz. LDO1, LDO2, and LDO3 are stabilized using on-chip capacitors (100 pF), while LDO4 and LDO5 using external capacitors (20 μF). A charge pump is used to double the 1.5 V battery voltage and provide the input for LDO4 and LDO5. The clock signals for the charge pump are generated using a current-mode relaxation oscillator.

II. Measurement Results

Figure 5A:
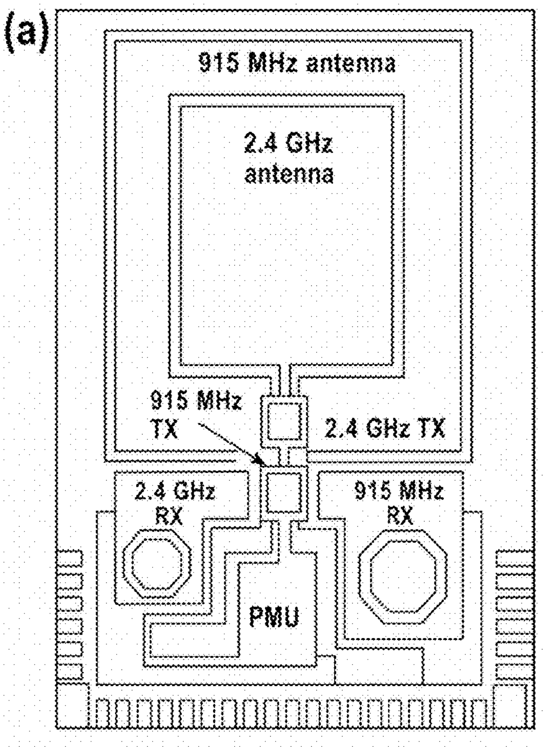
FIGS. 5A and 5B: (A) Chip micrograph. (B) Block-level diagram of the measurement setup for uplink (devices that connect using black and red cables) and downlink (devices that connect using black and blue cables) communications.
Figure 5B:
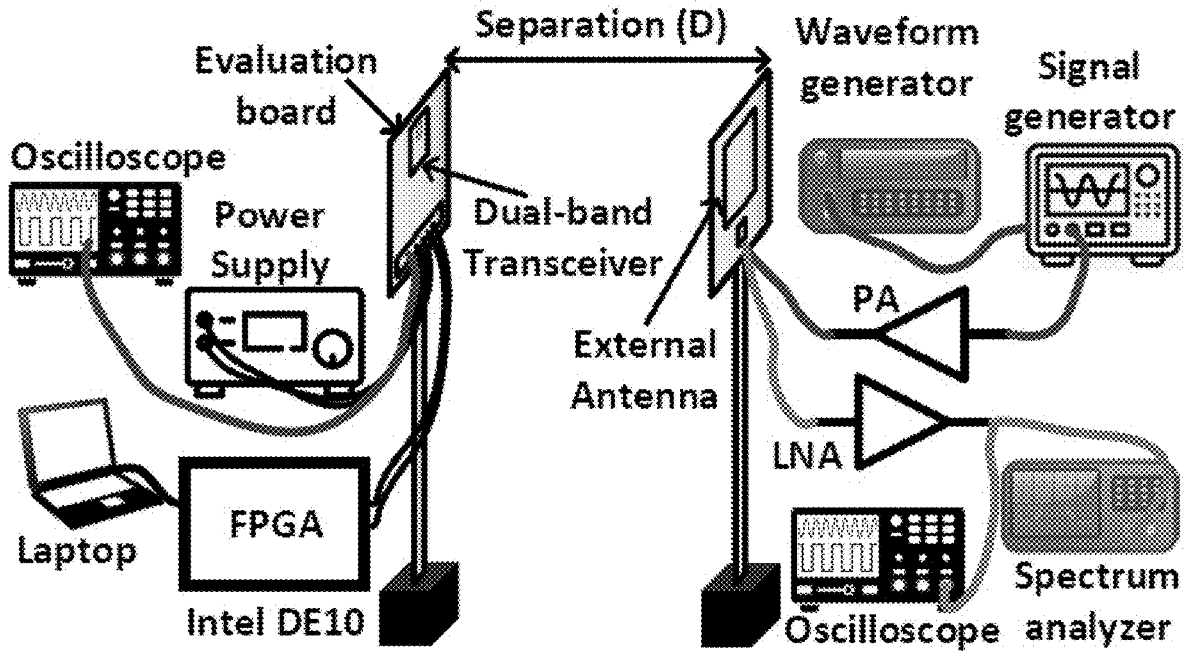

A prototype dual-band TRX has been fabricated in 180 nm CMOS (FIG. 5(A)). The block-level diagram of the measurement setup to test uplink (UL) and downlink (DL) is shown in FIG. 5(B). A 915 MHz loop antenna was utilized as the external antenna for the 915 MHz UL and DL measurements. For 2.4 GHz UL and DL, the external antenna was a wideband Vivaldi antenna and a 2.4 GHz loop antenna, respectively.

Figure 6A:
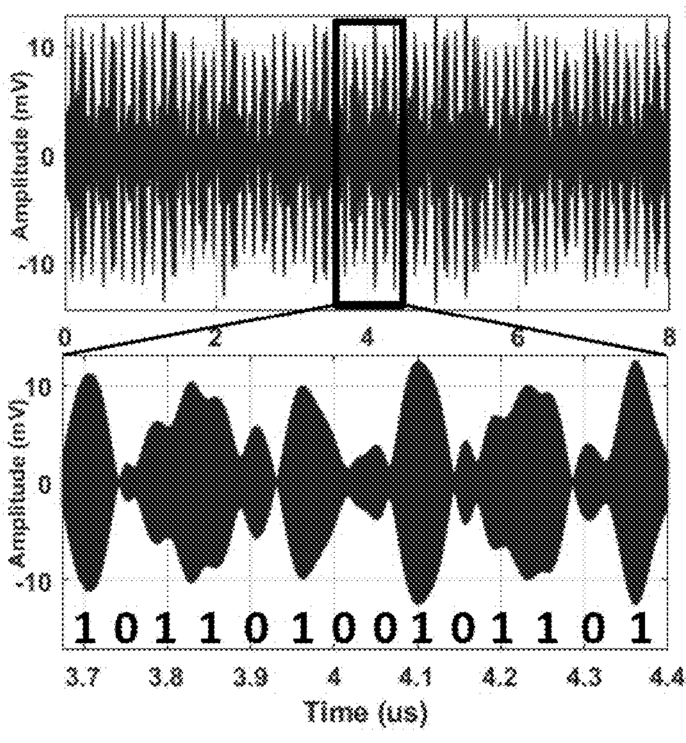
FIGS. 6A, 6B, 6C, and 6D: On air measurements: Measured uplink transient waveforms (at the external antenna) of the (A) 915 MHz OOK and (B) 2.4 GHz OOK communications. Measured downlink transient waveforms (at the on-chip receiver) of the (C) 915 MHz OOK and (D) 2.4 GHz OOK communications.
Figure 6B:
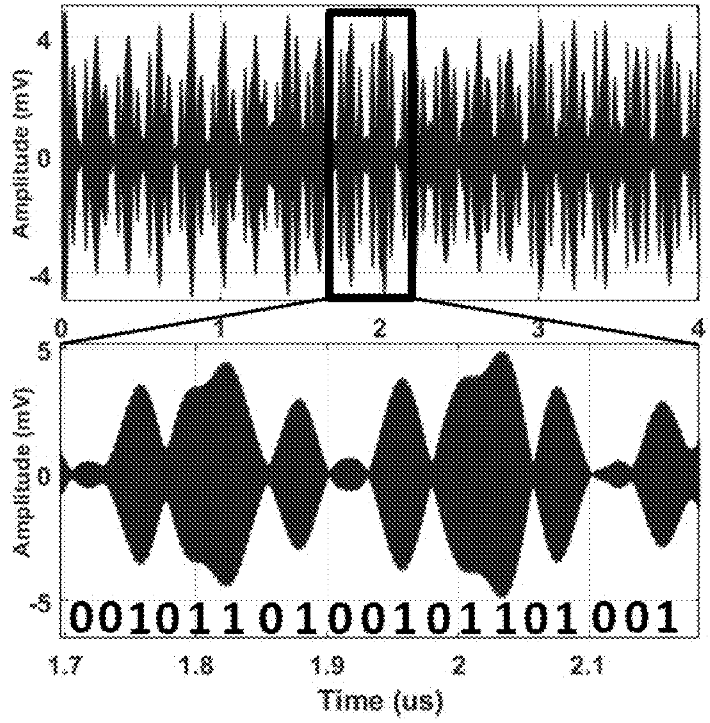

For the UL, the transmitted signals from the chip are first received at the external loop antenna, then amplified, and finally captured by an oscilloscope. This data is post-processed using MATLAB. FIG. 6(A) shows the post-processed received signal when the 915 MHz TX transmits a bitstream 01101001 (OOK) at 20 Mb/s with the external receiver place 30 cm away. The TX power consumption is 1.25 mW, which leads to energy efficiency of 62 pJ/b. FIG. 6(B) shows the corresponding results for the 2.4 GHz TX, with an energy efficiency of 35 pJ/b at 40 Mb/s (communication distance is 38 cm).

Figure 6C:
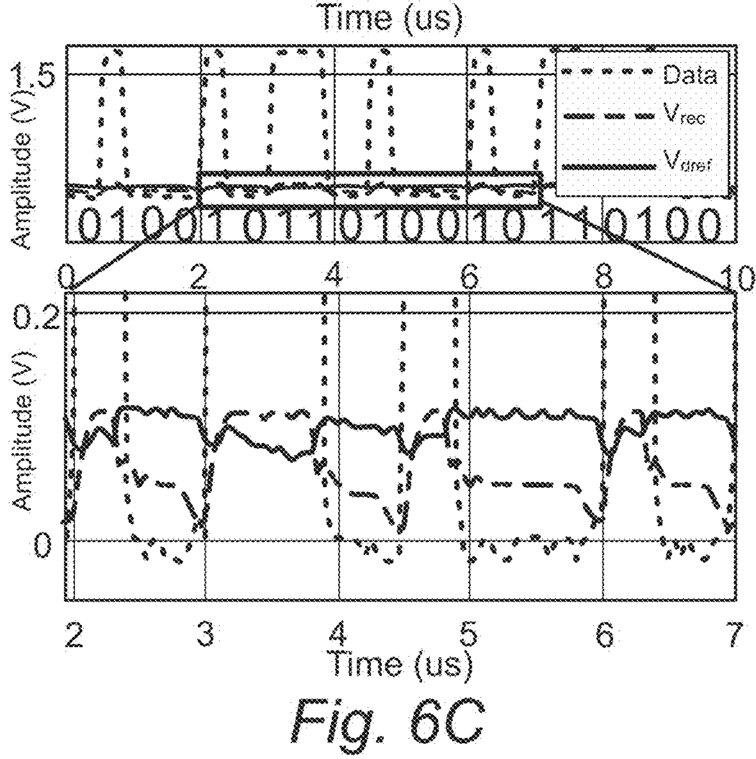
Figure 6D:
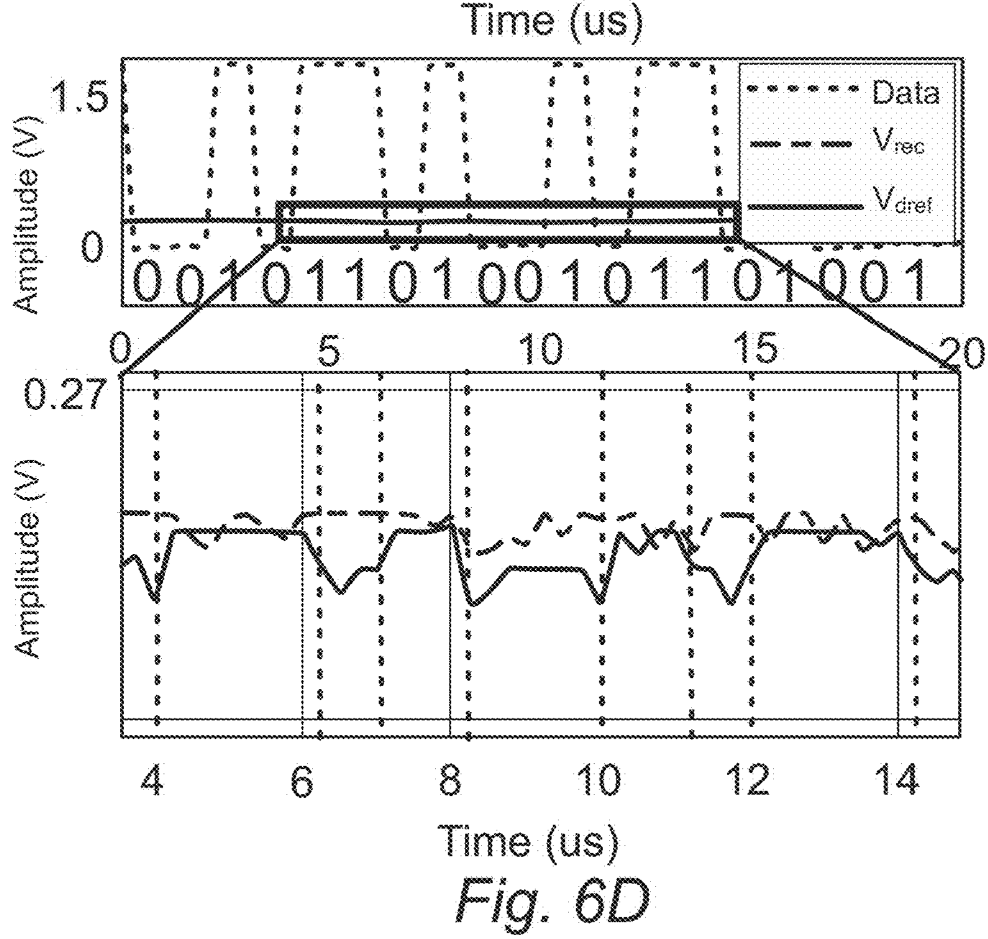
Figure 7A:
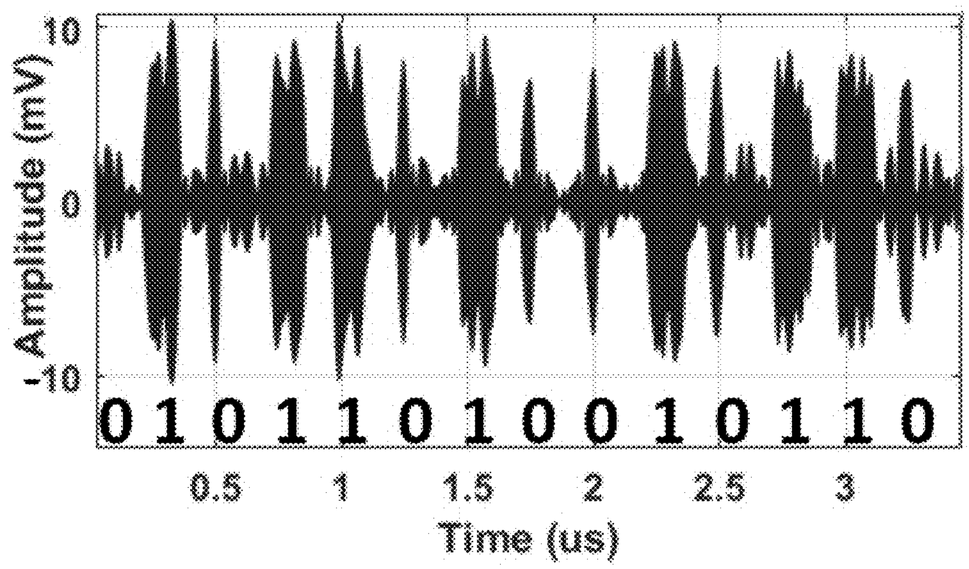
FIGS. 7A and 7B: On-air Measurement for OOK-PWM: Measured transient waveform for (A) 2.4 GHz UL and (B) 915 MHz DL (clock CLK, Vreg, and Data).
Figure 7B:
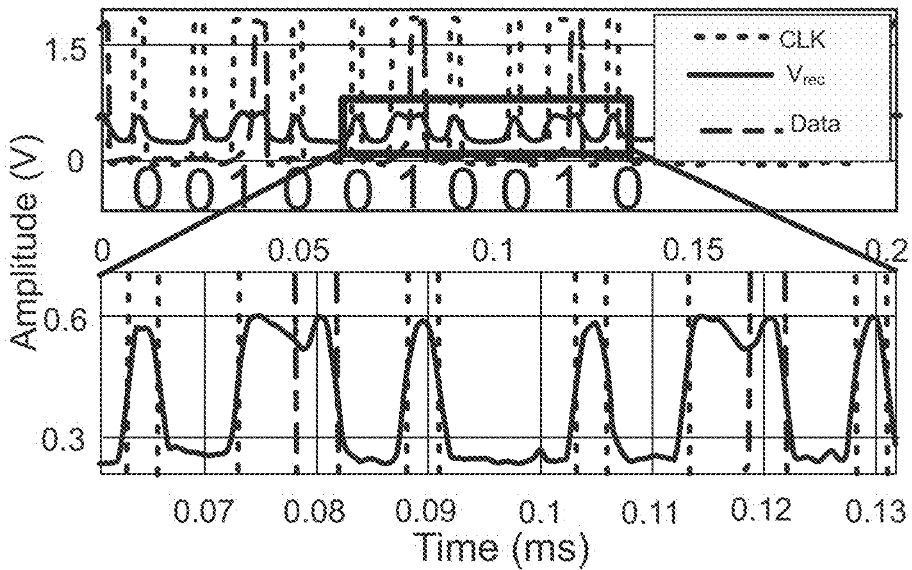
Figure 8A:
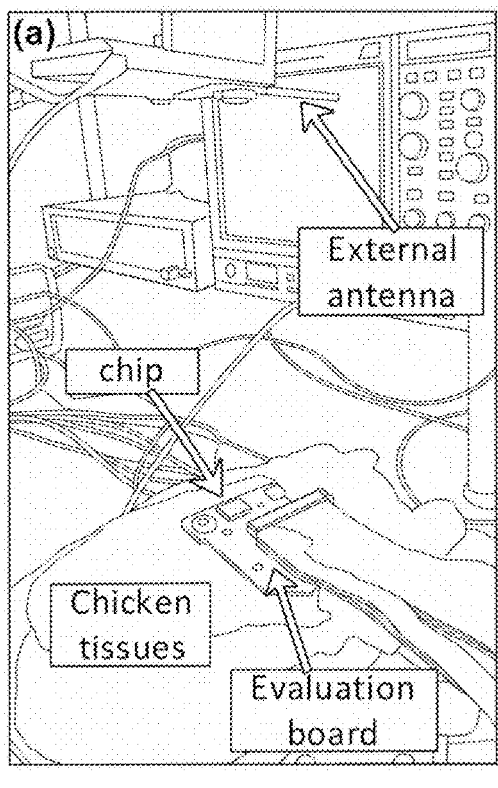
FIGS. 8A, 8B, 8C, 8D, 8E, and 8F: Setups to demonstrate the (A) wearable and (B) implantable operations. Measurements as a wearable: (C) 2.4 GHz UL and (D) 915 MHz DL signals. Measurements as an implant: (E) 2.4 GHz UL and (F) 915 MHz DL signals.
Figure 8B:
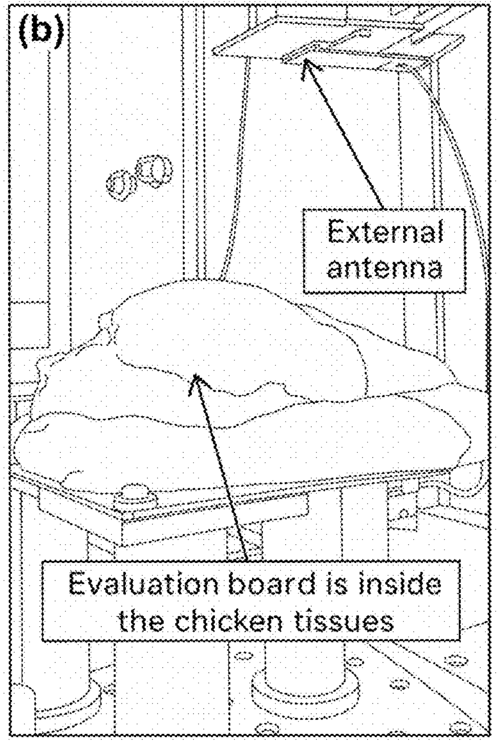
Figure 8C:
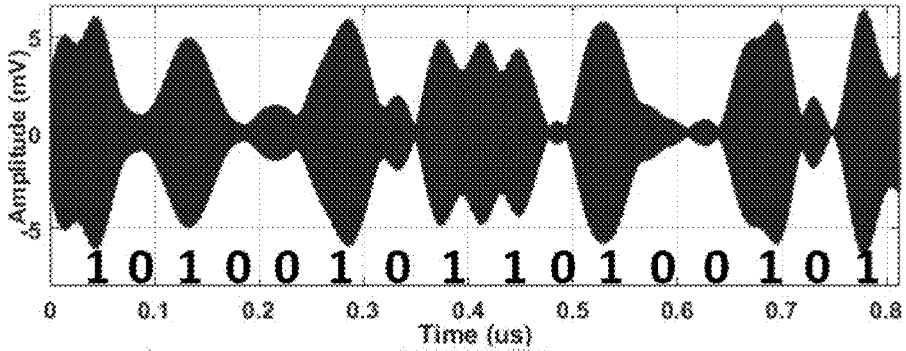
Figure 8D:
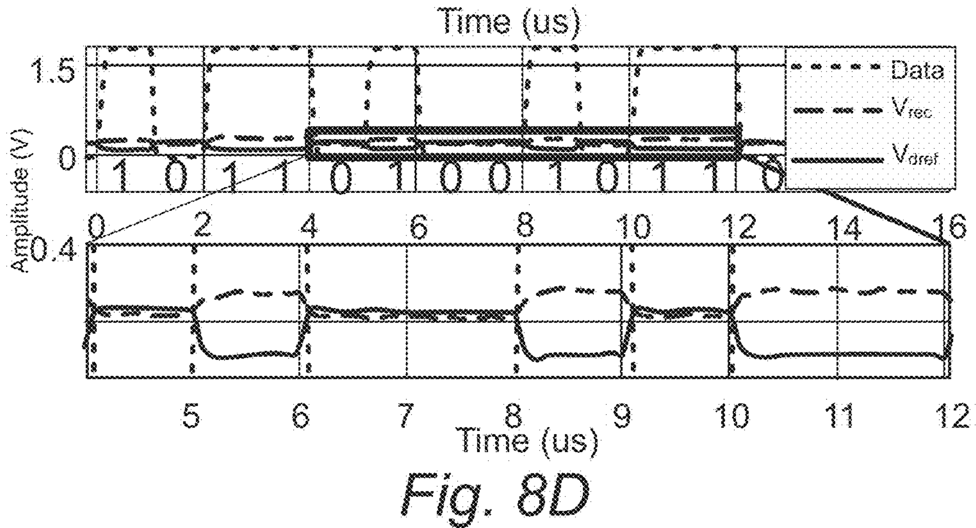
Figure 8E:
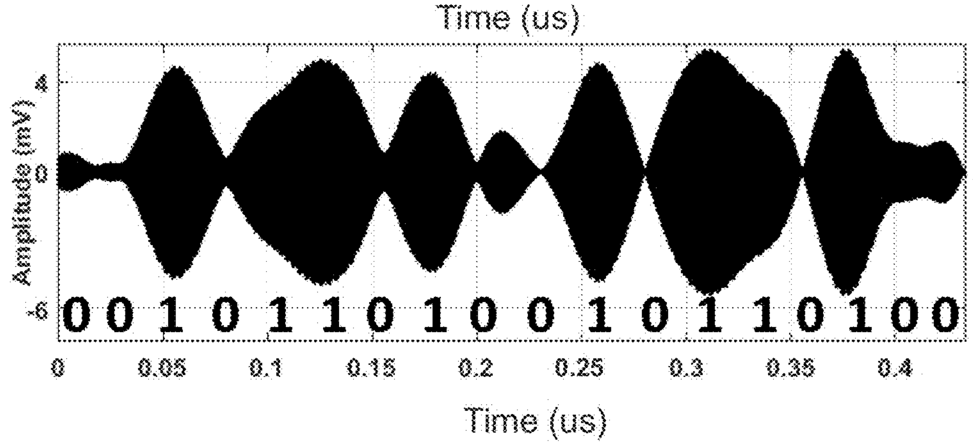
Figure 8F:
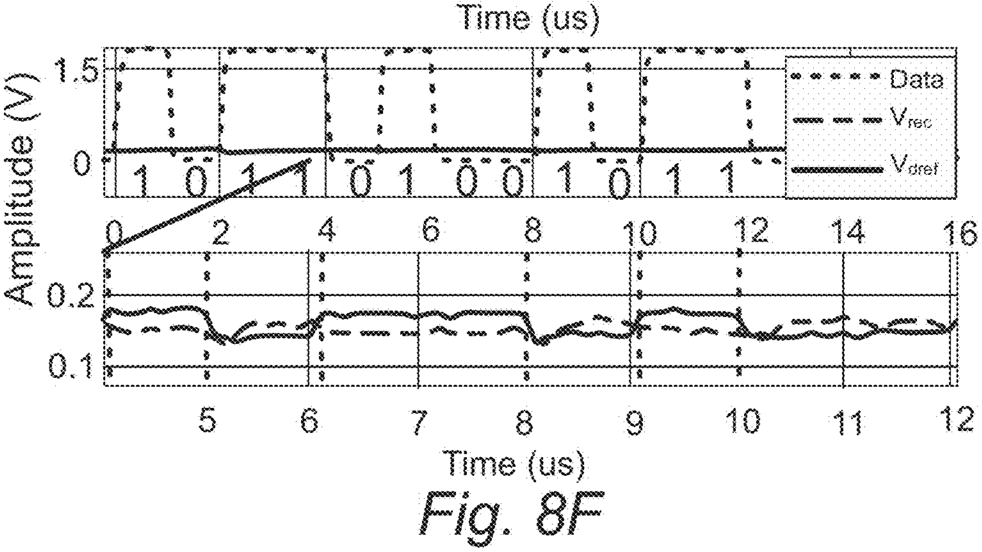

For the DL, the outputs of the on-chip RXs are captured directly in the oscilloscope. FIG. 6(C) shows the decoded signal for 915 MHz communication at 2 Mb/s where the distance between the two antennas is 11 cm. The figure also shows the variation of rectified output Vrec and dynamic reference Dref. The power consumption of the 915 MHz RX is measured to be 4 μW resulting in 2 pJ/b energy efficiency. FIG. 6(D) shows the DL results for 2.4 GHz link (1 Mb/s, 1 cm distance, 4 μW of power consumption) with 4 pJ/b of energy efficiency. The 2.4 GHz downlink can also achieve 100 kbps at 2 cm distance. FIG. 7(A) shows the post-processed UL signal for OOK-PWM modulation at 2.4 GHz (4 Mb/s, 28 cm distance, 1 mW of power) with energy efficiency of 270 pJ/b. FIG. 7(B) shows the decoded data, Vrec, and clock (CLK, DOOK) signals for 915 MHz OOK-PWM modulated DL (75 kb/s, 9 cm distance). The TRX has been fully tested emulating wearable and implantable operations (both bands, UL and DL). FIG. 8 shows only one case of each. To emulate wearable operation, the chip is placed on top of fresh animal tissue (FIG. 8(A)). FIG. 8(C shows the 2.4 GHz UL signal (20 Mb/s, 14 cm on air). The 915 MHz DL signals are shown in FIG. 8 (D) (1 Mb/s, 3.5 cm on air). To demonstrate implantable operation, the chip is placed inside the animal tissue (FIG. 8(B)). FIG. 8(E) shows the 2.4 GHz UL signal at the external antenna (40 Mb/s, 6 cm on air and 1 cm of tissue). The 915 MHz DL signals are shown in FIG. 8(F) (1 Mb/s, 2 cm on air and 1 cm of tissue). The dual-band TRX is capable of simultaneous transmission and reception using both frequency bands. As an implantable TRX, the 915 MHz and 2.4 GHz TXs achieved 16 Mb/s and 20 Mb/s of data rates when both TXs operate simultaneously. The total power consumption is 2.35 mW. The on-air distances are 11 cm and 6 cm for 915 MHz and 2.4 GHz links, respectively, with the chip 1 cm underneath the chicken tissue. The resulting energy efficiency is 67 pJ/b. The simultaneous reception has been tested on air by placing the 915 MHz and 2.4 GHz antennas 7 cm and 0.75 cm away from the chip, respectively. The data rates of the 915 MHz and 2.4 GHz DLs are 100 b/s and 2 Kb/s, respectively. Table I compares the dual-band TRX with the state of the art.

III. Conclusion

This work reports a dual-band TRX with mutually coupled on-chip antennas for implantable and wearable devices in 180 nm CMOS. To the best of our knowledge, this is the first implementation of such TRX capable of bidirectional communication in implantable and wearable devices with simultaneous transmission (or reception) at both frequency bands. This is achieved by utilizing mutually coupled on-chip antennas, LC oscillator-based TXs, and rectifier-based RXs. The fabricated prototype occupies an area of 2.41.9 mm$^2$ and achieves maximum data rates of 40 Mb/s for UL and 2 Mb/s for DL, up to 38 cm of range, and less than 70 pJ/b of energy efficiencies for different communication scenarios. The chip can be integrated with sensors on a flexible PCB to design a fully wireless miniaturized implantable/wearable device.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

[1] S. A. Mirbozorgi, H. Bahrami, M. Sawan, L. A. Rusch, and B. Gosselin, "A single-chip full-duplex high speed transceiver for multi-site stimulating and recording neural implants," IEEE Transactions on Biomedical Circuits and Systems, vol. 10, no. 3, pp. 643-653, 2016.

[2] M. Konijnenburg et al., "22.1 a 769 w battery-powered single-chip SoC with BLE for multi-modal vital sign health patches," in 2019 IEEE Int. Solid-State Circuits Conference—(ISSCC), 2019, pp. 360-362.

[3] H. Bhamra et al., "A subcubic millimeter wireless implantable intraocular pressure monitor microsystem," IEEE Transactions on Biomedical Circuits and Systems, vol. 11, no. 6, pp. 1204-1215, 2017.

[4] H. Bhamra, Y. W. Huang, Q. Yuan, and P. Irazoqui, "An ultra-low power 2.4 GHz transmitter for energy harvested wireless sensor nodes and biomedical devices," IEEE Transactions on Circuits and Systems II: Express Briefs, vol. 68, no. 1, pp. 206-210, 2021.

[5] S. Y. Lee, P. H. Cheng, C. F. Tsou, C. C. Lin, and G. S. Shieh, "A 2.4 GHz ISM band OOK transceiver with high energy efficiency for biomedical implantable applications," IEEE Transactions on Biomedical Circuits and Systems, vol. 14, no. 1, pp. 113-124, 2020.

[6] B. Chatterjee, A. Srivastava, D. H. Seo, D. Yang, and S. Sen, "A contextaware reconfigurable transmitter with 2.24 pj/bit, 802.15.6 NB-HBC and 4.93 pj/bit, 400.9 MHz medradio modes with 33.6% transmit efficiency," in IEEE Radio Frequency Integrated Circ. Symposium, 2020, pp. 75-78.

[7] H. Rahmani and A. Babakhani, "A 1.6 mm3 wirelessly powered reconfigurable fdd radio with on-chip antennas achieving 4.7 pJ/b TX and 1 pJ/b RX energy efficiencies for medical implants," 2020 IEEE Custom Integrated Circuits Conference (CICC), pp. 1-4, 2020.

[8] Z. Safarian and H. Hashemi, "Wideband multi-mode CMOS VCO design using coupled inductors," IEEE Transactions on Circuits and Systems I: Regular Papers, vol. 56, no. 8, pp. 1830-1843, 2009.

What is claimed is:

1. A dual-band implantable/wearable device including:

a transceiver comprising:

a first on-chip antenna;

a second on-chip antenna, the first on-chip antenna and the second on-chip antenna being mutually coupled;

a receiver including a dual receiver chain having a first receiver chain and a second receiver chain, the first receiver chain being in electrical communication with the first on-chip antenna and configured to operate within a first frequency band and the second receiver chain being in electrical communication with the second on-chip antenna and configured to operate within a second frequency band;

a dual-band dual-port LC oscillator-based transmitter in electrical communication with the first on-chip antenna and the second on-chip antenna and configured transmit data within the first frequency band and/or the second frequency band; and a power management unit configured to supply power to the receiver and the dual-band dual-port LC oscillator-based transmitter; and a circuit board attached to the transceiver, the circuit board including any combination of external sensors, capacitors, controller units, and a single battery, wherein the transceiver is configured to time-multiplex the first on-chip antenna and the second on-chip antenna to transmit and receive data.

2. The dual-band implantable/wearable device of claim 1 configured for simultaneous transmission or reception in both frequency bands.

3. The dual-band implantable/wearable device of claim 1, wherein the dual-band dual-port LC oscillator-based transmitter includes a mutually coupled dual-band oscillator in which the first on-chip antenna and the second on-chip antenna operate as oscillator inductors.

4. The dual-band implantable/wearable device of claim 1 wherein the transceiver is configured to be interconnected to with external sensors, capacitors, controller units, and a single battery.

5. The dual-band implantable/wearable device of claim 1 configured such that external devices can request data using either the first frequency band or the second frequency band.

6. The dual-band implantable/wearable device of claim 5 wherein an external controlling unit is configured to initiates controlling signals to extract sensing data from external sensors following a request for data, wherein extracted data directly modulates the dual-band dual-port LC oscillator-based transmitter to communicate with external devices.

7. The dual-band implantable/wearable device of claim 1 configured to support both on-off keying with pulse width modulation (OOK-PWM) and standard OOK modulation.

8. The dual-band implantable/wearable device of claim 1 wherein the first frequency band is a 915 MHz band and the second frequency band is a 2.4 GHz band.

9. The dual-band implantable/wearable device of claim 1 wherein the dual-band dual-port LC oscillator-based transmitter directly feeds oscillator signals to the first on-chip antenna and the second on-chip antenna without using a separate power amplifier, thereby reducing both power consumption and chip area compared to a PA+oscillator architecture.

10. The dual-band implantable/wearable device of claim 1 wherein the first receiver chain and the second receiver chain each independently include a switch, a matching network, a rectifier, a first decoder, and a second decoder arranged in the order indicated and in electrical communication.

11. The dual-band implantable/wearable device of claim 10 wherein each rectifier is a cascade of four cross-connected differential rectifiers.

12. The dual-band implantable/wearable device of claim 10 wherein OOK data is recovered at the first decoder by comparing rectified output with a dynamic reference generated by averaging this output using a low-pass filter with a Schmitt-trigger following the comparator to decrease noise sensitivity.

13. The dual-band implantable/wearable device of claim 10 wherein for OOK-PWM, an output of the first decoder is fed into the second decoder to be first integrated throughout a pulse width and then compared with a predefined threshold voltage, a comparator in the second decoder outputs '1' or '0' based on integrated pulse duration.

14. The dual-band implantable/wearable device of claim 10 wherein the power management unit includes a bandgap reference, five low-dropout (LDO) regulators (LDO1 to LDO5), a charge pump, and a relaxation oscillator.

15. A system for monitoring a subject comprising:

a dual-band implantable/wearable device including:

a transceiver comprising:

a first on-chip antenna;

a second on-chip antenna, the first on-chip antenna and the second on-chip antenna being mutually coupled;

a receiver including a dual receiver chain having a first receiver chain and a second receiver chain, the first receiver chain being in electrical communication with the first on-chip antenna and configured to operate within a first frequency band and the second receiver chain being in electrical communication with the second on-chip antenna and configured to operate within a second frequency band;

a dual-band dual-port LC oscillator-based transmitter in electrical communication with the first on-chip antenna and the second on-chip antenna and configured transmit data within the first frequency band and/or the second frequency band; and a power management unit configured to supply power to the receiver and the dual-band dual-port LC oscillator-based transmitter; and a circuit board attached to the transceiver, the circuit board including any combination of capacitors, controller units, and a single battery; and at least one external device attached to the subject and in electrical communication with the dual-band implantable/wearable device, wherein the at least one external device is configured to request data using either the first frequency band or the second frequency band.

16. The system of claim 15, wherein the external device is a drug delivery system.

17. The system of claim 15, wherein the external device is a neural interface.

18. The system of claim 15, wherein the external device is a blood pressure sensor, a heart rate sensor, an ECG, a vital sign sensor, and/or an intraocular pressure sensor.

19. The system of claim 15, wherein the dual-band implantable/wearable device is configured for simultaneous transmission or reception in both frequency bands.

20. The system of claim 15, wherein the dual-band implantable/wearable device is in wireless communication with the at least one external device.

21. The system of claim 15, wherein the dual-band implantable/wearable device is in wireless communication with a computing device.

22. A dual-band implantable/wearable device including:

a transceiver comprising:

a first on-chip antenna;

a second on-chip antenna, the first on-chip antenna and the second on-chip antenna being mutually coupled;

a receiver including a dual receiver chain having a first receiver chain and a second receiver chain, the first receiver chain being in electrical communication with the first on-chip antenna and configured to operate within a first frequency band and the second receiver chain being in electrical communication with the second on-chip antenna and configured to operate within a second frequency band;

a dual-band dual-port LC oscillator-based transmitter in electrical communication with the first on-chip antenna and the second on-chip antenna and configured transmit data within the first frequency band and/or the second frequency band; and a power management unit configured to supply power to the receiver and the dual-band dual-port LC oscillator-based transmitter; and a circuit board attached to the transceiver, the circuit board including any combination of external sensors, capacitors, controller units, and a single battery, wherein the dual-band dual-port LC oscillator-based transmitter directly feeds oscillator signals to the first on-chip antenna and the second on-chip antenna without using a separate power amplifier, thereby reducing both power consumption and chip area compared to a PA+oscillator architecture.

* * * * *